United States Patent [19]
Burzio et al.

[11] Patent Number: 5,817,470
[45] Date of Patent: Oct. 6, 1998

[54] IMMOBILIZATION OF ANTIGENS TO SOLID SUPPORT BY THE MUSSEL ADHESIVE POLYPHENOLIC PROTEIN AND THE METHOD FOR USE THEREIN

[75] Inventors: Luis O. Burzio; Veronica A. Burzio, both of Valdivia, Chile

[73] Assignee: Sociedad Biotecnologica Collico Limitada, Valdivia, Chile

[21] Appl. No.: 402,489

[22] Filed: Mar. 10, 1995

[51] Int. Cl.$^6$ .......... G01N 33/53; G01N 33/569; G01N 33/537; G01N 33/543

[52] U.S. Cl. .............. 435/7.9; 435/4; 435/7.1; 435/7.91; 435/7.92; 435/7.93; 435/7.94; 435/7.95; 435/174; 435/175; 435/176; 435/177; 435/178; 435/179; 435/180; 435/961; 436/518; 436/523; 436/524; 436/525; 436/526; 436/527; 436/528; 436/529; 436/530; 436/531

[58] Field of Search .......... 435/4, 7.1, 7.9–7.95, 435/174–180, 961; 436/518, 523–531

[56] References Cited

U.S. PATENT DOCUMENTS

| | | | |
|---|---|---|---|
| 4,446,231 | 5/1984 | Self | 435/7.1 |
| 4,585,585 | 4/1986 | Waite . | |
| 5,015,677 | 5/1991 | Benedict et al. | 524/17 |
| 5,024,933 | 6/1991 | Yang et al. | 435/6 |
| 5,108,923 | 4/1992 | Benedict et al. | 435/240.243 |
| 5,202,526 | 4/1993 | Maugh et al. . | |
| 5,242,808 | 9/1993 | Maugh et al. | 435/69.1 |
| 5,410,023 | 4/1995 | Burzio | 530/329 |

FOREIGN PATENT DOCUMENTS

243818A2  4/1987  European Pat. Off. .

OTHER PUBLICATIONS

Sigma Catalog p. 1255, 1993.
Practice and Theory of Enzyme Immunoassays; P. Tijssen 1985, pp. 297–329.
A Method for Attachment of Peptides to a Solid Surface with Enhanced Immunoreactivity; BioTechniques; vol. 13 No. 5 (1992) pp. 739–742.
Nature's Underwater Adhesive Specialist; Int. J. Adhesion and Adhesives; vol. 7 (1987) pp. 9–12.
Marine Bioadhesive: Projections in Medicine and Industry; Current Topics in Marine Biotechnology; pp. 353–356 (1989).
Purification of Adhesive Proteins From Mussels; Protein Expression and Purification; 1, 147–150 (1990).
Immunological Studies of the Polyphenolic Proteins of Mussels; Comp. Biochem. Physiol.; vol. 98B. No. 4, pp. 569–572 (1991).
Chimeric IgG–binding Receptors Engineered for Staphylococcal Protein A and Stretococcal Protein G; The Journal of Biological Chemistry; vol. 263, No. 9, Issue of Mar. 25, pp. 4323–4327 (1988).
$\alpha,\beta$–Dehydro–3,4–dihydroxyphenylalanine Derivatives; Potential Schlerotization Intermediates in Natural Composite Materials; Archives of Biochemistry and Biophysics; vol. 285, No. 1, Feb. 15, pp. 17–26, (1991).
Clinical Chemistry, vol. 36, No. 8, 1990, "A Decade of Development in Immunoassay Methodology", pp. 1408–1426.
Clinical Chemistry, vol. 40, No. 3, 1994, "Selected Strategies for Improving Sensitivity and Reliability . . . ", pp. 347–357.
Arch. Biol. Med. Exp 23, Burzio et al, "Bioadhesives: A biotechnological opportunity", pp. 173–178, 1990.
1994 Aldrich Chemical Company, Inc., "Chemists helping chemists", ordering information, p. 1271.

*Primary Examiner*—Sheela Huff
*Attorney, Agent, or Firm*—Jacobson, Price, Holman & Stern, PLLC

[57] ABSTRACT

This invention is related to a process for the enhanced immobilization of a ligand to solid supports to be used for a biochemical detection method. The enhanced immobilization of the ligand was obtained by coating the surface of the solid support with the adhesive polyphenolic protein isolated from mussels. The bound ligand is reacted with a solution containing an antiligand whereby the antiligand becomes bound to the immobilized ligand. After removing the excess or unbound antiligand, the antiligand bound to the immobilized ligand is detected by using an enzyme-linked immunoassay.

34 Claims, 1 Drawing Sheet

METHOD A

METHOD B

IMMOBILIZATION OF ANTIGENS TO SOLID SUPPORT BY THE MUSSEL ADHESIVE POLYPHENOLIC PROTEIN AND THE METHOD FOR USE THEREIN

TECHNICAL FIELD OF THE INVENTION

This invention is related to a process for the enhanced immobilization of a ligand to solid supports to be used for a biochemical detection method. The enhanced immobilization of the ligand was obtained by coating the surface of the solid support with an adhesive polyphenolic protein isolated from mussels. The bound ligand is reacted with a solution containing an antiligand whereby the antiligand becomes bound to the immobilized ligand. After removing the excess or unbound antiligand, the antiligand bound to the immobilized ligand is detected by using an enzyme-linked immunoassay.

BACKGROUND OF THE INVENTION

This invention is related to a detection method in which a ligand is immobilized on a surface previously coated with the adhesive polyphenolic protein isolated from mussels. Thereby, the ligand is reacted with an antiligand and the bound antiligand is measured by enzyme-linked immunoassay.

The term ligand and antiligand are used herein to denote a pair of molecules which are capable to recognize each other specifically. Examples of ligands are antigens, haptens, hormones and other cellular components. Examples of antiligands are antibodies and receptors. Biochemical detection methods based in the specific interaction between ligand and antiligand are described in U.S. Pat. No. 4,446,231, which is incorporated herein by reference.

Examples of detection methods based on the interaction between ligand and antiligand are the enzyme-linked immunosorbent assay or ELISA, radioimmunological, immunofluorescent, or immunobioluminescent methods. The enzyme-linked immunoassay is a powerful technique for the determination of antibodies and antigens in the field of research and clinical medicine. Several variations have been described (Tijssen, P. (1985) in *Practice and Theory of Enzyme Immunoassays* (R. H. Burdon and P. H. van Knippenberg, eds., Elsevier Science Publishers, Amsterdam). Examples are the determination of specific antibodies in human and animals fluids. This method comprises in the immobilization of an antigen to a solid support which will react to and binds to the specific antibodies. The antigen is bound to a solid surface, preferably a multi-well test plate of polystyrene, by chemical means (covalent linkage) or by the most frequently used physiochemical adsorption and hydrophobic interaction. The following step is to block all the available sites left on the surface after the binding of the antigens, a step that is usually performed by incubation of the microplate wells with a protein solution such as bovine serum albumin (BSA). Then the human or animal fluid or dilutions of it is added to each well of the microplate and incubated under specific conditions. After washing the plates with saline solutions, the amount of antibody bound to the immobilized antigen is measured with an anti-antibody (also referred to as the second antibody) which is chemically bound or conjugated to a particular enzyme (for example phosphatase or peroxidase). Following the washing of the plates with a saline solution to eliminate all the unbound enzyme conjugated anti-antibody, the enzyme reaction is allowed to proceed by adding a corresponding chromogenic soluble substrate, dissolved in the adequate solutions regarding ionic strength, pH and other properties.

After a short period of incubation, the reaction is stopped and the intensity of the color developed is measured with special spectrophotometers. To enhance the sensitivity of the final detection step, several variations have been developed, such as amplified enzyme reactions (U.S. Pat. No. 4,446,231). Under these conditions, it is possible to measure and to detect the presence of antibodies in human or animal fluids, as well as amount of monoclonal antibodies in hybridoma culture medium.

One limitation of this procedure is the amount of antigen bound or adsorbed to the solid surface. The final amount of antigen strongly bound to the surface of the plate depends on the molecular characteristics of the antigens, the properties of the solid support, the concentration of the antigen in the solution as well as the characteristics of the buffer used to dissolve the antigen used to coat or to activate the surface. In general, only a small fraction of the antigen present in the coating solution is adsorbed to the surface. To enhance the amount of immobilized antigens, chemical covalent attachment has been developed in (Tijssen, P. (1985), *Practice and Theory of Enzyme Immunoassays* R. H. Burdon and P. H. van Knippenberg, eds.), Elsevier Science Publishers, Amsterdam; D. C. Leahy, D. O. Shah and J. A. Todd (1992) *BioTechniques,* 13: 738–743).

Mussels produce an adhesive protein known as polyphenolic protein or mussel adhesive protein *Mytilus edulis* adhesive protein comprises the sequence Ala-Lys-Pro-Ser-Tyr-Pro-Pro-Ser-Tyr-Lys as set forth in the "Sequence Listing" as SEQ ID. No. 1, wherein proline may be substituted with hydroxy proline, serine may be substituted with threonine and tyrosine may be substituted with DOPA in *Mytilus edulis.* (U.S. Pat. No. 4,585,585, issued Apr. 29, 1986 to Waite; *Int. J. Adhesion and Adhesives,* 7: 9–14 (1987)). These proteins are able to bind to different surfaces such as slate, ceramics, various plastics and metals (*Int. J. Adhesion and Adhesives,* 7: 9–14 (1987)). We have discovered that these adhesive proteins are also able to mediate the immobilization of enzymes, e.g. to β-galactosidase, glass or plastic surfaces (*Current Topics in Marine Biotechnology,* S. Miyachi, I. Karube and Y. Ishida, eds), Japanese Soc. Marine Biotechnology, Tokyo, pp. 353–356 (1989)). The polyphenolic protein used is substantially rich in amino acids selected from the group consisting of lysine, glycine, proline and 3,4-dihydroxyphenylalanine, among other amino acids. By "substantially rich in amino acids" is meant that the amount of the particular amino acid is over 7%. However, the content of lysine, proline and glycine are over 10% depending on the polyphenolic protein. On the other hand, DOPA fluctuated from 7% to 17%. For example, the heptapeptide of *Aulacomya ater* contains 1 DOPA out of 7 amino acids, or 14% content. However, there is about 7.9% DOPA in the total polyphenolic protein of *Aulacomya ater.* An effective amount of polyphenolic protein is an amount necessary to coat the surface of the solid support to form a membrane or film such that even at a low concentration of antigen or antibody, the presence of the antigen or antibody can be detected. A preferable amount is 0.1–1.0 $\mu$g of the polyphenolic protein per well of the microtiter plates. A more preferable amount is 1.0–1.5 $\mu$g. Solid support includes polystyrene, polypropylene, polycarbonate, Nylon, glass and metal such as steel.

SUMMARY OF THE INVENTION

Based on the properties of the mussel adhesive proteins, we have discovered a method to enhance the immobilization of antigens to a solid surface. Each well of a multi-well plate or microtiter plate was coated with a solution containing 0.1

μg to 0.5 μg of the polyphenolic protein or adhesive protein isolated from the mussels *Aulacomya ater, Choromytilus chorus, Mytilus californianus* and *Mytilus edulis chilensis* (*Protein Expression and Purification*, 1: 147–150 (1990)) or *Aulacomya ater* (*Comparative Biochem. Physiol.*, 98B: 569–572 (1991). *Aulacomya ater* contains polyphenolic protein with a relative consensus of Ala-Gly-DOPA-Gly-Gly-Val-HO-Lys (SEQ ID No. 2 wherein DOPA and HO-Lys are represented as "Xaa" which is different from the decapeptide of *Mytilus edulis chilensis* and *Choromytilus chorus*. After coating, different amounts of antigen in a solution containing 10 mM sodium phosphate buffer (pH 7.5) and 150 mM sodium chloride (PBS) were added and incubated for 1 hour at room temperature. After discarding the antigen solution, the wells were blocked with a solution containing 1% of bovine serum albumin (BSA) in PBS (PBS-BSA). The plates were then incubated for 2 hours at room temperature with a solution of a monoclonal or polyclonal antibody for the antigen (dissolved in PBS-BSA), washed with PBS containing 0.02% Tween 20, and finally incubated with an anti-antibody conjugated to phosphatase or peroxidase. After adding the substrate, the color reaction was measured with a microplate spectrophotometer. It was discovered that when a low concentration of antigen was used to activate wells of regular microtiter plates, the intensity of the color reaction was practically no different to the color intensity of control wells not incubated or activated with the antigen. In contrast, if the same low concentration of antigen was used to activate wells previously coated with the mussel adhesive protein, the reading or color reaction was several times superior than wells coated with the adhesive protein but not incubated with the antigen. It is important to mention that the same results were obtained using phosphatase or peroxidase conjugates anti-antibodies or second antibodies, which indicates that the method was independent of the detection method used. The immobilized antigen may be a hormone, viral antigen or protein, such as Protein A, Protein G or recombinant Protein A/G. (Eliasson M. et al., *J. Biol. Chem.*, 263: 4323–4327 (1988)). One embodiment of the present invention is the use of the polyphenolic protein from mussel in method A, which is used to determine the presence of antibodies in animal fluid or to determine the titer of monoclonal antibodies.

Another embodiment is method B, the "sandwich ELISA" which is used to determine a variety of molecules or antigens, such as hormones, virus, bacteria, fungi, cytokines, growth factors, drugs, etc. The method has been improved by immobilizing first Protein A or Protein G and probably recombinant protein A/G to the microtiter well, previously coated with the mussel adhesive. The polyphenolic protein or adhesive protein from the mussels substantially enhanced the immobilization of Protein A to the wells. Similarly, the immobilization of Protein G and recombinant Protein A/G is enhanced. Under these conditions, the binding of the first antibody is enhanced by about 100 times. It was indeed quite unexpected and represented a major improvement in biochemical assay technology. But more importantly, all the antibody molecules are bound to the Protein A by the Fc regions, or in other words, all the molecules of antibodies are functional. This permits a great saving in the amount of the first antibody needed to coat the wells. This procedure is followed by the addition of a fluid containing the putative antigens, and then a complementary antibody conjugated with a particular enzyme to generate color. FIGS. 1 and 2 show a diagram of method A and method B.

DESCRIPTION OF PREFERRED EMBODIMENTS

Figure 1:
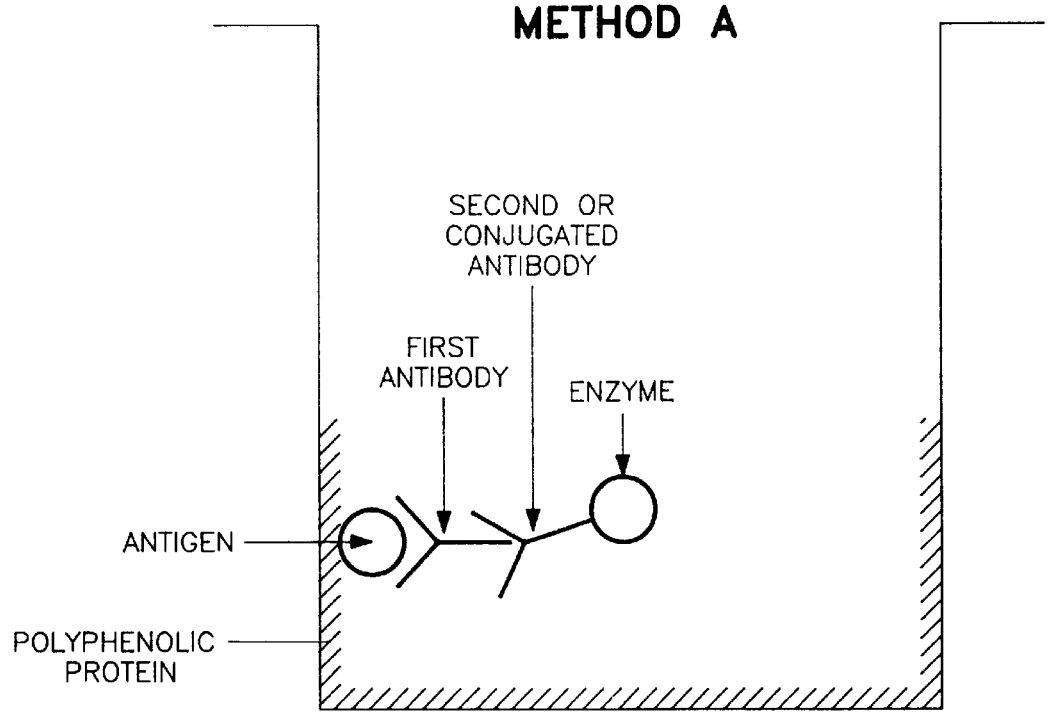
FIG. 1 shows the scheme of the bioassay to determine the presence of antibodies in animal fluids.
Figure 2:
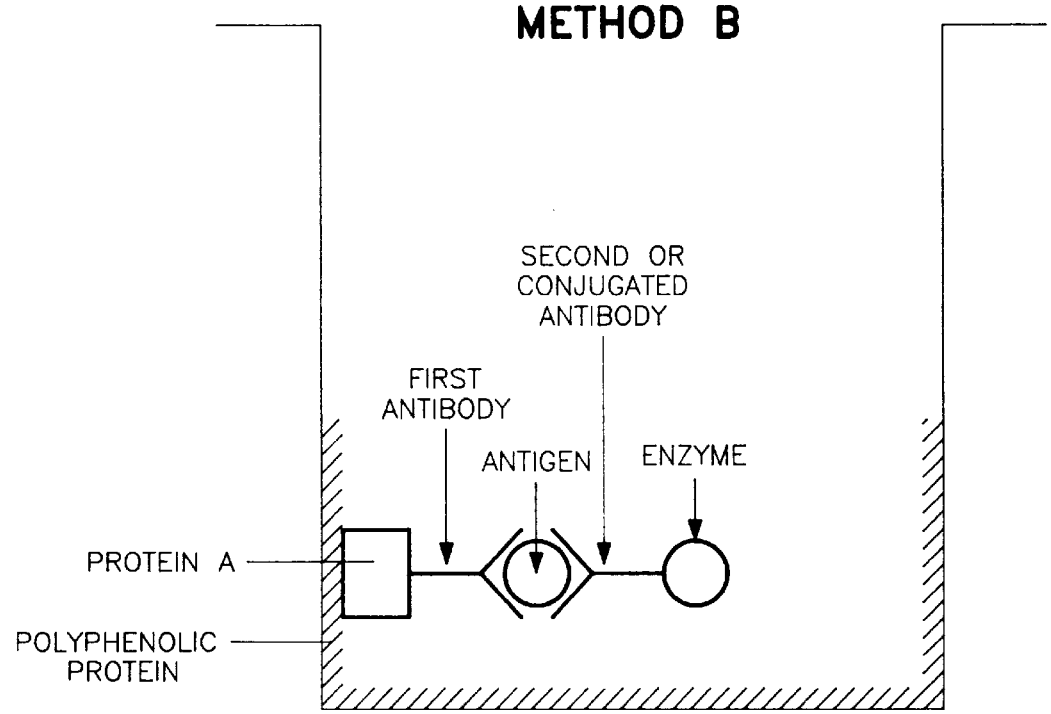
FIG. 2 shows the scheme of the bioassay referred to as the "sandwish" ELISA to determine the presence of antigens.

In any chemical or biochemical reaction, an important component is the "noise" of the system due to non-specific binding of the various components of the system. In the immunoassay developed by us with the mussel adhesive protein, this means, for example, binding of the antibody or antiligand to sites in the surface of the microliter wells other than its specific binding to the immobilized antigen. Also, the anti-antibody conjugated to a particular enzyme or second antibody can bind to sites other than the specific binding of the first antibody. These non-specific bindings are particularly significant when the concentration of the tested antibody is low. Therefore, an important parameter of these methods is that the "signal to noise" ratio should be high. In other words, the ratio between the absorbance of the wells with a positive sample (a fluid containing the specific antibody or first antibody) and the absorbance of a control well (without antigen or without the first antibody), has to be high. The method discovered by us using the mussel adhesive protein has a better "signal to noise" ratio than the conventional methods.

In nature, the adhesive protein of mussel forms the byssus, a complex of threads and adhesive plaques. This structure is the result of extensive cross-linking between the polyphenolic protein and other components of the byssus. The mechanism of cross-linking is unknown at the present time, but there are strong indications that the residues of 3,4-dihydroxyphenylalanine (DOPA) are involved in this reaction. It is important to mention that these polyphenolic proteins are rich in DOPA residues (*Int. J. Adhesion and Adhesives*, 7: 9–14 (1987); *Protein Expression and Purification*, 1: 147–150 (1990); *Comparative Biochem. Physiol.*, 98B: 569–572 (1991). It has been postulated that the oxidation of these DOPA residues to the o-quinone by a mussel tyrosinases or cathecol oxidase, could be involved in the cross-linking reaction. More recently, it has been suggested that a novel derivative of DOPA, α, β-dehydro-DOPA, might also be involved in the reaction (*Arch. Biochem. Biophys.*, 285: 17–26 (1991). We discovered that oxidation of the film of adhesive protein adsorbed to the well surface of microtiter plate enhanced even further the amount of immobilized antigen. Therefore, the procedure described was modified as follows: after coating the wells with the adhesive polyphenolic protein, a solution containing from 0.01 mM to 0.02 mM sodium periodate in PBS was added and incubated for 15 minutes at room temperature. After removing the periodate solution and washing the wells with PBS, the solution of antigen was added and incubated at room temperature for 1 hour. The rest of the procedure was the same as already described. Under these conditions it was discovered that the oxidation of the adhesive polyphenolic protein with sodium periodate enhanced even further the immobilization of the antigen. Moreover, the signal to noise ratio was also improved.

Immunoassay Procedure

This is an example of how the immunoassay using the polyphenolic protein from the mussels *Choromytilus chorus, Mytilus edulis chilensis* or *Aulacomya ater* was performed, and formed the basis of the following Examples.

Human chorionic gonadotrophin (hCG) was obtained from Sigma Chemical Co. The HIV-I antigen gp120 was obtained from Bios Chile, I.G.S.A. (Santiago, Chile). Monoclonal antibodies against hCG (7G8-2 and 2G1-2) were from Bios Chile. A monoclonal antibody against gp120 (IAM 120-2G12) was obtained from Viral Testing Systems Corporation (Houston, Tex.). Polystyrene microtiter plates were obtained from Nunc, Corning and Dynatec. The polyphenolic proteins of *Aulacomya ater, Choromytilus chorus* and *Mytilus edulis* were purified as described before (*Protein Expression and Purification*, 1: 147–150 (1990); *Comparative Biochem. Physiol.*, 98B: 569–572 (1991)).

To each well of microtiter plates, 0.01 ml containing 0.1 μg to 0.5 μg of adhesive polyphenolic protein from the mussels in 0.1% acetic acid was added together with 0.09 ml of 100 mM sodium phosphate (pH 7.5), and incubated at room temperature for 15 min. After emptying the plate and washing a couple of times with distilled water, 0.1 ml of solution of 10 mM sodium phosphate (pH 7.5) plus 0.15M sodium chloride (PBS) containing different amounts of antigen was added and incubated at room temperature for 1 hour. The antigen solution was discarded and the plates were blocked by adding 0.3 ml of a solution containing 1% BSA in PBS and incubated for 2 hours at room temperature. The plates were emptied and 0.1 ml of the monoclonal antibody diluted in 1% BSA in PBS was added and incubated for 2 hours at room temperature or 1 hour at 37° C. The solution was discarded and the wells washed 3 times with PBS containing 0.02% Tween 20. Then, 0.1 ml of the corresponding anti-IgG (anti-human or anti-mouse) antibody, conjugated with alkaline phosphatase or horseradish peroxidase diluted in 1% BSA in PBS was added to each well and incubated for 1 hour at room temperature. The wells were washed 4 to 6 times with PBS containing 0.02% Tween 20, and then the solution containing the substrate was added and incubated according to the optimal conditions for each enzyme. For alkaline phosphatase, the substrate used was p-nitrophenyl phosphate and color was allowed to develop for 30 min. at 37° C. The reaction was stopped with 1M sodium hydroxide and the plate was read at 405 nm in a MultisKan MK II spectrophotometer. For peroxidase, the substrate was o-phenylenediamine (OPD) and the reaction was carried out at room temperature for 5 to 10 minutes. The reaction was stopped with 0.3N sulfuric acid and the plate was read at 492 nm in the above spectrophotometer.

EXAMPLE 1

This example illustrates the effect of coating with different amounts of mussel adhesive protein on the reading and signal/noise ratio obtained with a fixed amount of hCG per well and a monoclonal antibody (7G8-2). Wells in triplicate were coated with the amount of polyphenolic protein from *Choromytilus chorus* as indicated in Table 1. Then the plates were incubated for 1 hour with 50 nanogram of hCG in PBS, washed 3 times with PBS, and blocked with 1% BSA in PBS. After incubation for 1 hour at room temperature with 0.1 ml of the monoclonal antibody (2 μg/ml) diluted in 1% BSA in PBS, the plates were washed four times with PBS containing 0.02% Tween 20. After washing, 0.1 ml of anti-mouse IgG conjugated with alkaline phosphatase diluted 1:2,000 in 1% BSA in PBS was added and incubated for 1 hour. The enzyme reaction was developed and the color intensity was measured at 405 nm.

TABLE 1

| Amount of Polyphenolic protein for coating μg | Absorbance at 405 mm | Signal/Noise |
|---|---|---|
| 0.0 | 0.160 | 3.33 |
| 0.05 | 0.510 | 9.80 |
| 0.10 | 0.840 | 16.15 |
| 0.2 | 1.160 | 22.30 |
| 0.5 | 1.110 | 21.34 |

Coated or uncoated wells and without hCG have an absorbance at 405 nm of 0.052 and 0.048, respectively. The signal to noise ratio referred to as the ratio between the reading with 50 ng of hCG vs. the reading without hormone.

Table 1 shows that with 0.2 μg of polyphenolic protein (PP) per well, the absorbance was about 7 times higher than the absorbance of the uncoated (no adhesive protein) control wells. Also the signal to noise ratio was superior in the coated wells than the uncoated controls. Similar results were obtained when the adhesive protein isolated from *Aulacomya ater* was compared with the protein of *Choromytilus chorus* as shown in Table 2. The adhesive protein isolated from *Mytilus edulis chilensis* also enhanced the immobilization of hCG.

TABLE 2

| | ABSORBANCE AT 405 nm | |
|---|---|---|
| Coated with | Activated with 50 ng hCG | No hCG |
| No coating | 0.120 | 0.057 |
| PP of *A. ater* | 1.456 | 0.060 |
| PP of *C. chorus* | 1.510 | 0.085 |

The amount of PP used to coat the well was 0.25 μg.

EXAMPLE 2

This example illustrates the effect of coating with the polyphenolic protein on the amount of hCG adsorbed to the well incubated with different amounts of the hormone. The wells were coated with 0.2 μg of polyphenolic protein as described before and then with different amounts of hCG in 0.1 ml in PBS as indicated in Table 3. The rest of the procedure was the same described in EXAMPLE 1. The monoclonal antibody for hCG (7G8-2) was used at a concentration of 10 μg/ml in PBS-BSA, and the anti-mouse IgG conjugated with alkaline phosphatase was used at a dilution of 1:3,000 in PBS-BSA. The results in Table 3 show that, at the same amount of hCG per well, the readings of 405 nm were superior than the readings of the wells uncoated with the polyphenolic protein. In other words, much less antigen was necessary to obtain the same reading, which indicates that the hormone was more efficiently bound to the coated wells. The same results were obtained with other monoclonal antibodies for hCG.

TABLE 3

| | ABSORBANCE AT 405 nm | |
|---|---|---|
| Amount of hCG (ng/well) | Coated with 0.2 μg of PP | Uncoated |
| 1.0 | 0.071 | 0.008 |
| 5.0 | 0.488 | 0.082 |

TABLE 3-continued

| | ABSORBANCE AT 405 nm | |
|---|---|---|
| Amount of hCG (ng/well) | Coated with 0.2 μg of PP | Uncoated |
| 10.0 | 0.727 | 0.129 |
| 50.00 | 1.045 | 0.200 |
| 100.0 | 1.075 | 0.279 |

The monoclonal antibody 7G8-2 was used. The anti-mouse IgG was conjugated with phosphatase.

EXAMPLE 3

Similar results were obtained when the assay was carried out with the protein gp120 of HIV-I as shown in Table 4. The amount of polyphenolic protein used to coat was 0.25 μg per well and the amounts of gp120 are indicated in the Table 4. The anti-gp120 was a human monoclonal antibody (from Viral Testing Systems Inc.) and was used at a concentration of 1 μg/ml in PBS-BSA. The anti-human IgG (BRL) conjugated with peroxidase was used at a dilution of 1:4,000 in PBS-BSA.

TABLE 4

| | ABSORBANCE AT 492 nm | |
|---|---|---|
| Amount of gp120 (ng/well) | Coated with 0.2 μg of PP | Uncoated |
| 10 | 0.220 | 0.030 |
| 50 | 0.780 | 0.170 |
| 100 | 1.100 | 0.250 |
| 500 | 1.350 | 0.360 |

The monoclonal against gp120 was 120-dh56. The anti-human IgG was conjugated to peroxidase.

Similar to the results with hCG, the results in Table 4 show that much less gp120 was required to obtain the same reading at 492 nm. In other words, the coating with polyphenolic protein enhanced the immobilization of two quite different antigens (a hormone and a viral protein).

EXAMPLE 4

The immunoassays described in EXAMPLES 2 and 3 are useful to measure the amount of antibodies, specific for the antigen, present in body fluid as well as in the culture medium of hybridoma used for the preparation of monoclonal antibodies. This example illustrates the use of the present invention to evaluate the amount of monoclonal antibodies against the antigen gp 120 of HIV-I.

The wells were coated with 0.2 μg of polyphenolic protein as described before. After coating, the wells were incubated for 2 hours at room temperature with 50 ng of gp120 in 0.1 ml of PBS, and blocked with BSA as described. Then the wells were incubated for 1 hour with the anti-gp120 monoclonal antibody (Viral Testing Systems Inc.), at the dilutions in PBS-BSA indicated in Table 5. After washing and incubating with the anti-human IgG conjugated with peroxidase (BRL), the color reaction was developed with OPD as substrate and the plate read at 492 nm. The results in Table 5 indicated that in the coated wells, the reading was superior at all the dilutions of the anti-gp120 tested when compared with the uncoated wells at the same dilutions. Moreover, the signal to noise ratio was also superior in the first case. Similar results were obtained with plates coated with hCG and tested with different dilutions of the monoclonal 7G8-2.

TABLE 5

| | ABSORBANCE AT 492 nm | |
|---|---|---|
| Amount of anti-gp 120 (μg/ml) | Coated with 0.2 μg of PP | Uncoated |
| 0.25 | 0.460 | 0.095 |
| 0.50 | 0.710 | 0.160 |
| 1.0 | 1.020 | 0.220 |
| 2.5 | 1.230 | 0.310 |

The anti-gp120 was the monoclonal 120-dh56. The anti-human IgG was conjugated with peroxidase.

EXAMPLE 5

This example illustrates the effect of treatment of the adsorbed polyphenolic protein with sodium periodate on the enhancement of the binding of the antigen gp120. The wells were coated with 0.2 μg of polyphenolic protein as described in previous examples. After emptying the plate, 0.1 ml of 10 μM sodium periodate was added and incubated at room temperature for 10 min. The plate was emptied, washed with PBS and incubated with 0.1 ml containing 100 ng of gp120 for 1 hour at room temperature as described previously. The wells were then blocked with PBS-BSA and incubated with 0.1 ml of the anti-gp120 monoclonal diluted in PBS-BSA. After washing with the PBS-Tween 20 solution 3 times, 0.1 ml of the anti-human IgG conjugated with peroxidase was added and incubated for 1 hour at room temperature. The color development with OPD was the same as described before.

As shown in Table 6, the amount of gp120 adsorbed to the wells previously coated with PP was much higher than the uncoated controls. Moreover, pretreatment of the PP-coated surface with 10 μM sodium periodate enhanced even further the absorbance at 492 nm. The oxidative agent did not change in a marked way the reading of the uncoated well. The blank (without gp120) exhibited low reading and was unaffected by the treatment with sodium periodate (Table 6).

TABLE 6

| | ABSORBANCE AT 492 nm | | | |
|---|---|---|---|---|
| Amount of | 0.0 μg PP | | 0.25 μg PP | |
| gp 120 (ng/well) | −NaIO4 | +NaIO4 | −NaIO4 | +NAIO4 |
| 0 ng | 0.077 | 0.074 | 0.096 | 0.074 |
| 100 ng | 0.162 | 0.130 | 0.932 | 1.328 |
| 0 ng | 0.076 | 0.069 | 0.089 | 0.070 |
| 100 ng | 0.159 | 0.119 | 0.949 | 1.341 |

The concentration of sodium periodate (NaIO4) used was 10 μM and a total volume of 100 μl. The incubation was for 10 min. at room temperature.

EXAMPLE 6

This example illustrates the effect of coating wells with the mussel adhesive polyphenolic protein on the immobilization of Protein A. Protein A has the property to bind antibodies especially the IgG fraction. Therefore, immobilization of Protein A to the solid support will mediate the binding of IgG for biochemical detection methods based on specificity of antibodies, for example to hormones. The wells were coated with 0.3 μg of polyphenolic protein as described before and then incubated for 1 hour at room temperature with 0.1 ml containing different amounts of Protein A in PBS as described before. Then, 0.1. ml containing a dilution of 1:5,000 of rabbit serum in 1% BSA in PBS was added to each well and incubated for 2 hours at room temperature. The plates were washed four times with PBS containing 0.02% Tween 20, and incubated with 0.1 ml of anti-rabbit IgG conjugated with peroxidase diluted 1:3,000 in 1% BSA in PBS. The plates were again washed with PBS containing 0.02% Tween 20 followed by the development of the enzyme reaction. The color intensity was measured at 492 nm.

TABLE 7

| Amount of Protein A (ng/well) | ABSORBANCE AT 492 nm | |
|---|---|---|
| | +PP | −PP |
| 0 | 0.078 | 0.068 |
| 5 | 0.146 | 0.073 |
| 10 | 0.350 | 0.070 |
| 25 | 0.870 | 0.114 |
| 50 | 1.750 | 0.187 |
| 100 | 2.178 | 0.312 |

The above wells were coated with 0.5 µg of polyphenolic protein of *A. ater* in 0.1 ml. After activation with the indicated amount of Protein A, the wells were incubated with rabbit serum diluted 1:5,000. The goat anti-rabbit IgG conjugated with peroxidase was used at a dilution of 1:3,000.

As shown in Table 7, the coating with the adhesive protein enhanced the immobilization of the Protein A to the plate surface, and consequently the binding of the IgG fraction.

While this invention has been disclosed and described with respect to preferred embodiments, it will be understood by those skilled in the art that various changes and modifications may be made without departing from the spirit and scope of the invention as set forth in the following claims.

We claim:

1. A method for immobilization of an immunologically reactive ligand on a surface of a solid support comprising:
coating a surface of a solid support with an adhesive polyphenolic protein, isolated from mussels, so as to form a membrane thereon;
incubating the membrane coated support with a buffer;
contacting a suspension of an immunologically reactive ligand with a surface of the membrane; wherein the amount of adhesive protein added per well of the solid support is between 0.1–0.5 µg in a volume of 100 µl.

2. The method according to claim 1, further comprising treating the membrane with an oxidative agent.

3. The method according to claim 2, wherein the oxidative agent is sodium periodate.

4. The method according to claim 1, wherein the polyphenolic protein used is substantially rich in amino acids selected from the group consisting of lysine, glycine, proline and 3,4-dihydroxyphenylalanine.

5. The method according to claim 4, wherein the substantially rich amount of amino acid is more than 7%.

6. The method according to claim 1, wherein the adhesive protein is isolated from mussels selected from a group consisting of *Choromytilus chorus, Aulacomya ater, Mytilus californianus* and *Mytilus edulis chilensis*.

7. The method according to claim 1 wherein the solid support is polystyrene selected from the group consisting of polypropylene, polycarbonate, Nylon, glass and metal.

8. The method according to claim 1 wherein the solid support is polystyrene, selected from the group consisting of polypropylene, polycarbonate, Nylon, glass and metal.

9. The method according to claim 1 further comprising employing the coated membranes to determine the amount of antibodies in human and animal fluids.

10. A biochemical detection method for detecting antiligand present in human and animal fluids comprising:
   coating a solid support with a membrane comprising an adhesive polyphenolic protein isolated from mussels;
   the amount of adhesive protein added per well of the solid support is between 0.1–0.5 $\mu$g in a volume of 100 $\mu$l;
   immobilizing a ligand with the membranous coating of the adhesive protein;
   reacting the immobilized ligand with a solution containing an antiligand, wherein the antiligand binds to the immobilized ligand;
   separating the unbound antiligand from the bound antiligand;
   measuring the presence of ligand by detecting the bound antiligand to the immobilized ligand by a method selected from the group consisting of enzyme linked immunosorbentassay (ELISA), radioimmunology, immunofluorescent and immunobioluminescent methods.

11. The method according to claim 10, wherein the polyphenolic protein used is substantially rich in amino acids selected from the group consisting of lysine, proline and 3,4-dihydroxyphenylalanine.

12. The method according to claim 11, wherein the immobilized ligands are selected from the group consisting of hormones, viral antigen and protein.

13. The method according to claim 12, wherein the hormone is hCG.

14. The method according to claim 12, wherein the antigen is selected from the group consisting of Protein A and HIV-I gp120.

15. The method according to claim 12 wherein the viral antigen is HIV-1 gp 120.

16. The method according to claim 12 wherein the immobilized ligand is a protein selected from the group consisting of Protein A, Protein G and recombinant Protein A/G.

17. The method according to claim 16 wherein the immobilized Protein A, Protein G or Protein A/G is useful for immobilization of immunoglobulin.

18. The method according to claim 10 wherein the ligand is selected from the group consisting of antigen, hapten, hormones and other cellular components.

19. The method according to claim 18 wherein the oxidative agent is sodium periodate.

20. The method according to claim 11 wherein the antiligand is selected from the group consisting of antibody and receptor.

21. In a biochemical assay system in which an immunologically reactive ligand binds to a substrate, the improvement comprising the substrate having thereon, a membranous coating of an adhesive polyphenolic protein isolated from mussels, in an amount between 0.1–0.5 $\mu$g in a volume of 100 $\mu$l, wherein said polyphenolic protein enhances immobilization of an immunologically reactive ligand to the substrate.

22. The assay system of claim 21, wherein the polyphenolic protein is isolated from mussels selected from the group consisting of *Choromytilus chorus, Aulacomya ater, Mytilus californianus* and *Mytilus edulis chilensis*.

23. The assay system according to claim 21, wherein the polyphenolic protein used is substantially rich in amino acids selected from the group consisting of lysine, glycine, proline and 3,4-dihydroxyphenylalanine.

24. The assay system according to claim 21, wherein the immobilized immunologically reactive ligand is selected from the group consisting of antigen, hapten, hormones and other cellular components.

25. The assay system according to claim 24, wherein the antigen is selected from the group consisting of Protein A and HIV-I gp120.

26. The assay system according to claim 24, wherein the immobilized antigens are selected from the group consisting of hormones, viral antigen and protein.

27. The assay system according to claim 26, wherein the hormone is hCG.

28. The assay system according to claim 21, further comprising an oxidative agent.

29. The assay system according to claim 28, wherein the oxidative agent is sodium periodate.

30. The assay system of claim 21 wherein the system detects amounts of antibody present in a biological sample.

31. A solid support for use in a biochemical assay, having a membranous coating thereon, said coating consisting essentially of an effective amount of an adhesive polyphenolic protein isolated from byssus gland of mussels, wherein said polyphenolic protein enhances immobilization of an immunologically reactive ligand to the solid support, wherein said effective amount of adhesive protein is between 0.1–0.5 $\mu$g in a volume of 100 $\mu$l.

32. The solid support according to claim 31, in the form of a plate made from polystyrene selected from the group consisting of polypropylene, polycarbonate, Nylon, glass and metal.

33. The solid support according to claim 31, further treated with an oxidative agent.

34. The solid support according to claim 33, wherein the oxidative agent is sodium periodate.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 10 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:1:

Ala Lys Pro Ser Tyr Pro Pro Ser Tyr Lys
1               5                   10

( 2 ) INFORMATION FOR SEQ ID NO:2:

( i ) SEQUENCE CHARACTERISTICS:
( A ) LENGTH: 7 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:2:

Ala Gly Xaa Gly Gly Val Xaa
1               5